United States Patent [19]

Keppler et al.

[11] Patent Number: 5,256,653
[45] Date of Patent: Oct. 26, 1993

[54] PHARMACEUTICAL PREPARATIONS CONTAINING PLATINUM COMPLEXES/PHOSPHONIC ACID LIQUID AND PROCESSES FOR THEIR USE

[75] Inventors: Bernhard Keppler, Schwetzingen; Helmut Blum, Duesseldorf, both of Fed. Rep. of Germany

[73] Assignee: Henkel Kommanditgesellschaft auf Aktien, Deusseldorf, Fed. Rep. of Germany

[21] Appl. No.: 675,209

[22] Filed: Mar. 26, 1991

Related U.S. Application Data

[63] Continuation of Ser. No. 399,467, Aug. 18, 1989, abandoned.

[30] Foreign Application Priority Data

Feb. 19, 1987 [CH] Switzerland .................. 00638/87

[51] Int. Cl.$^5$ .................. A61K 31/685; A61K 31/27; C07F 15/00; C07D 225/00
[52] U.S. Cl. .................................. 514/79; 514/80; 514/99; 514/102; 514/141; 514/492; 540/450; 556/18; 556/19; 556/137; 546/5; 548/402
[58] Field of Search .................. 556/627, 136, 140, 18, 556/137; 514/75, 102, 492, 29, 141; 548/5, 11, 12, 402, 403

[56] References Cited

U.S. PATENT DOCUMENTS

| | | | |
|---|---|---|---|
| 4,845,124 | 7/1989 | Kidani et al. | 514/492 |
| 4,870,070 | 9/1989 | Bitha et al. | 556/137 X |
| 4,882,447 | 11/1989 | Tsojihara et al. | 556/40 |
| 4,921,984 | 5/1990 | Nowatari et al. | 556/40 |

FOREIGN PATENT DOCUMENTS

0113508 7/1984 European Pat. Off. .
0155705 9/1985 European Pat. Off. .

OTHER PUBLICATIONS

Carter et al., Chemotherapy of Cancer, 2d edition, pp. 107–108 and 361–365 (1981).
T. G. Appleton, et al., *Inorganic Chemistry*, 1986, vol. 25, pp. 726–734.

Primary Examiner—Frederick E. Waddell
Assistant Examiner—T. J. Criares
Attorney, Agent, or Firm—Ernest G. Szoke; Wayne C. Jaeschke; Norvell E. Wisdom, Jr.

[57] ABSTRACT

Platinum complexes of the general formula I $$[(R^1NH_2)_nPt]_qY_mX_p \qquad (I)$$

in which Y is a phosphonic acid ligand, and the preparation thereof, are described. The platinum complexes are suitable as active substances in pharmaceuticals, in particular for controlling cancers.

20 Claims, No Drawings

PHARMACEUTICAL PREPARATIONS CONTAINING PLATINUM COMPLEXES/PHOSPHONIC ACID LIQUID AND PROCESSES FOR THEIR USE

CROSS REFERENCE TO RELATED APPLICATION

This application is a continuation of copending application Ser. No. 399,467 filed on Aug. 18, 1989, now abandoned, which was the U.S. National Stage of PCT Application EP88/00111 filed Feb. 15, 1988.

The invention relate to platinum complexes, process for the preparation thereof, and pharmaceuticals containing these. An essential structural element of the platinum complexes of the invention is the simultaneous presence of ligands containing N and phosphonic acid groups.

Phosphonic acids are employed not only in industry but also for medical purposes, cf. The Role of Phosphonates in Living Systems, CDC Press, Inc., Boca Raton, Fla. (1982); M. D. Francis et al., J. Chem. Educ 55 (12), 760–766 (1978).

It is known that certain phosphonic acids accumulate in bone and tumour tissue after intravenous administration. Thus, for example, Paget's disease of bone is treated with the disodium salt of 1-hydroxyethane-1,1-diphosphonic acid, cf. The Merck Index, Merck & Co., Inc., Rahway, N.J., USA (1983) 3812. The compound known under the INN of cisplatin, cis-diamminedichloroplatinum(II), is employed in particular for the treatment of testicular tumours, ovarian tumours or small-cell bronchial carcinomas.

It has now been found that platinum complexes of the general formula I $$[R^1NH_2)_nPt]_qY_mX_p \cdot TM \quad (I)$$

in which a) $R^1$ denotes hydrogen, $C_1$–$C_8$-alkyl, $C_1$–$C_8$-alkenyl, $C_4$–$C_8$-cycloalkyl or $C_4$–$C_8$-cycloalkyl-$C_1$–$C_4$-alkyl, each of which can be substituted one or more times by $C_1$–$C_4$-alkyl, $C_1$–$C_4$-alkoxy, hydroxyl, amino, halogen, amino-$C_1$–$C_2$-alkyl, hydroxyamino, carboxyl, $C_1$–$C_4$-alkoxycarbonyl, $C_4$–$C_8$-cycloalkyl, phenyl or phenoxy, it being possible for the substituents $C_4$–$C_8$-cycloalkyl, $C_4$–$C_8$-cycloalkyl-$C_1$–$C_4$-alkyl, phenyl and phenoxy in their turn to be substituted one or more times by hydroxyl, halogen, $C_1$–$C_4$-alkyl or $C_1$–$C_4$-alkoxy, Y denotes a group of the formula II $$(HO)_2P(O)—R^2 \quad (III)$$

in which $R^2$ is defined as $R^1$ with the exception of hydrogen and of nitrogen-containing meanings, it being possible for a further group $(HO)_2P(O)$— to be bonded to $R^2$, X denotes a singly negatively charged anion, n denotes the numbers I or 2, but the number 1 only if $R^1$ has a nitrogen functionality which is able to coordinate with the central metal Pt, m denotes the numbers 1 or 2, but the number 1 only if $R^2$ has a group $(HO)_2P(O)$— which is able to coordinate with the central metal Pt, and p denotes the numbers 0 or 2, but the number 2 only if Pt is present in oxidation state IV, and q denotes the number 1, b) Y denotes a group of the above formula II in which $R^2$ denotes a $C_1$–$C_4$-alkylamino-phosphono-methyl, 3-amino-1-phosphono-1-hydroxy-1-propyl, amino-p-hydroxymethyl-phosphono-methyl, iminobis (methylene-phosphono) or N,N-bis(methylene-phosphono)-amino group, $R^1$, X, n and p are as defined above, and q denotes the number 1, and m denotes the number 1, C) Y is bis-(dihydroxyphosphonylmethyl)-aminoacetic acid, $R^1$, X, n and p are as defined above, and q denotes the number 1, and m denotes the number 1, d) q the number 2, m the number 1 and Y has one of the above meanings, with the proviso that Y contains at least 2 phosphono groups, and $R^1$, X, n and p are as defined above, or e) n is the number 0 and q is the number 1, and Y has one of the above meanings, with the proviso that Y contains at least 2 phosphono groups, and X and p are as defined above and the salts thereof with pharmacologically acceptable acids and bases, have advantageous therapeutic effects which make them suitable for the treatment of cancers, especially of bone tumours, osteosarcomas and bone metastases, liver tumours and tumours of the reticuloendothelial system (RES).

Alkyl, alkenyl and alkoxy radicals according to the abovementioned definitions can be straight-chain or branched, with straight-chain radicals being preferred. Preferred halogen atoms are chlorine atoms.

Depending on the pH of the reaction mixture, the phosphonic acids are present in the reaction product as neutral ligands or as singly or doubly negatively charged ligands. In the former case the charge on the complex is balanced by the anion of an acid, for example chloride. In the case where negatively charged ligands are present the charge is balanced by the cation of a base, preferably of an alkali metal, in particular of sodium.

Furthermore, platinum complexes of the invention in which the ligands are arranged in the cis position are preferred.

Furthermore, platinum complexes of the invention which contain two phosphonic acid groups are preferred, with the vicinal and the geminal position of the phosphonic acid groups being preferred. Particularly preferred compounds contain two geminal phosphonic acid groups.

Furthermore, platinum complexes of the general formula I'

$$[(R^{1'}NH_2)_nPt]_qY'_mX'_p \quad (I')$$

in which a) $R^{1'}$ denotes hydrogen, $C_1$–$C_4$-alkyl, cyclohexyl, cyclohexyl-$C_1$–$C_2$-alkyl, each of which can be substituted one or more times by methyl, ethyl, methoxy, ethoxy, hydroxyl, amino, chlorine, aminomethyl, carboxyl, $C_1$–$C_2$-alkoxycarbonyl, cyclohexyl, phenyl or phenoxy, it being possible for the substituents cyclohexyl, cyclohexyl-$C_1$–$C_2$-alkyl, phenyl and phenoxy in their turn to be substituted one or more times by hydroxyl, chlorine, methyl or methoxy, Y' denotes a group of the formula II'

$$(HO)_2P(O)-R^{2'}$$

in which
- $R^{2'}$ is defined as $R^{1'}$ with the exception of hydrogen and of nitrogen-containing meanings, it being possible for another group $(HO)_2P(O)-$ to be bonded to $R^{2'}$,
- X' denotes chlorine, hydroxyl and singly negatively charged anions of pharmacologically acceptable carboxylic acids,
- n' denotes the numbers 1 or 2, but the number 1 only if $R^{1'}$ has a nitrogen functionality is which can be coordinated with the central metal Pt,
- m' denotes the numbers 1 or 2, but the number 1 only if $R^{2'}$ has a group $(HO)_2P(O)-$ which can be coordinated with the central metal Pt,
- p' denotes the numbers 0 or 2, but the number 2 only if Pt is present in oxidation state IV, and
- q' denotes the number 0, b) $R^{1'}$ is as defined above, and Y', X', n', m', p' and q' have the meanings specified in claim 1 under b, c, d and e, respectively, for Y. X, n, m, p and q, as well as the salts thereof with pharmacologically acceptable acids and bases, are preferred.

Furthermore, platinum complexes of the general formula II''

$$[(R^{1''}NH_2)_{n''} \ldots Pt]_{q''}Y''_{a''}Z''_{p''} \qquad (I'')$$

in which
a) $R^{1''}$ denotes hydrogen, ethyl, cyclohexyl, cyclohexylmethyl, each of which can be substituted once by methyl, methoxy, hydroxyl, amine or aminomethyl, Y'' denotes a group of the formula II''
$$(HO)_2P(O)-R^{2''}$$

in which
- $R^{2''}$ denotes $C_1$-$C_4$-alkyl which can be substituted one or more times by chlorine, hydroxyl, carboxyl and cyclohexyl and is substituted by another group $(HO)_2P(O)-$,
- X'' denotes chlorine, hydroxyl and singly negatively charged anions of pharmacologically acceptable carboxylic acids,
- n'' denotes the numbers 1 or 2, but the number 1 only if $R^{1''}$ has a nitrogen functionality which is able to coordinate with the central metal Pt,
- m'' denotes the numbers 1 or 2, but the number 1 only if $R^{2''}$ has a group $(HO)_2P(O)-$ which is able to coordinate with the central metal Pt,
- p'' denotes the numbers 0 or 2, but the number 2 only if Pt is present in oxidation state IV, and
- q'' denotes the number 0, or b) $R^{1''}$ is as defined above and Y'', X'', n'', m'', p'' and q'' have the meanings stated in claim 1 under b, c, d and e, respectively, for Y, X, n, m, p and q, as well as the salts thereof with pharmacologically acceptable acids and bases, are preferred.

Particularly advantageous are, furthermore, platinum complexes of the above general formula I, I' and I'' in which Y, Y' and Y'' denote phosphonic acids of the general formulae IV–VI $$R^4-C(R^5)(PO_3H_2)_2 \qquad (IV)$$

in which $R^4$ denotes $C_1$-$C_3$-alkyl, optionally hydroxyl-substituted $C_5$-$C_6$-cycloalkyl, phenyl, hydroxyphenyl, halogen, $R^5R^6N-(CH_2)_r-$, where $R^5$ and $R^6$, which can be identical or different, denote hydrogen and/or $C_1$-$C_3$-alkyl and r denotes a number from 2 to 4, or denotes $-CH(COOH)-CH_2-COOH$, and $R^5$ is hydrogen, hydroxyl, amino, mono- or di-$C_1$-$C_3$-alkylamino or $C_1$-$C_3$-alkyl, $$R^6-C(COOH)(R^7)(PO_3H_2) \qquad (V)$$

in which $R^6$ denotes hydrogen, $-CH_2-COOH$ or $-CH_2-CH_2-COOH$ and $R^7$ denotes hydrogen, $-CH_2-CH_2-COOH$ or $-CH_2-CH(COOH)-CH-CH_2-COOH$, it also being possible for $R^4$ and $R^5$ to form an azacycloalkane ring having 4–6 carbon atoms and, where appropriate, a $C_1$-$C_3$-alkyl substituent on the N atom, or $$R^8-N(CH_2-PO_3H_2)_2 \qquad (VI)$$

in which $R^8$ denotes $-CH_2-PO_3H_2$, $-CH_2-COOH$ or $-CH_2)_s-N(CH_2-PO_3H_2)_2$, where s is a number from 2 to 6,
and n, n', n'', q, q', q'', m, m', m''', X, X', X'', p, p', p'', $R^1$, $R^{1'}$ and $R^{1''}$ are as defined above,
as well as the salts thereof with pharmacologically acceptable acids and bases.

Furthermore, platinum complexes of one of the above general formulae in which the phosphonic acid ligand is 1-hydroxyethane-1, 1-diphosphonic acid or dichloromethanediphosphonic acid are preferred.

The phosphonic acids present in the platinum complexes of the invention are known and can be obtained by methods known per se. A corresponding statement applies to the amines $R^1NH_2$.

Examples of suitable phosphonic acids of the general formulae Y, Y' and Y'' are the following, including the salts thereof (the abbreviated names customary for these compounds are indicated in square brackets):
dichloromethanediphosphonic acid [Cl$_2$-MDP],
2-phosphonobutane-1,2,4-tricarboxylic acid (PBTC),
2-phosphonopropane-1,2,3-tricarboxylic acid (PPS),
1-phosphonopropane-1,2,3-tricarboxylic acid [PPT],
propane-2,2-diphosphonic acid (PDP),
1,1-diphosphonopropane-2,3-dicarboxylic acid (DPD),
1-hydroxyethane-1,1-diphosphonic acid [EHDP, also HEDP],
methylenediphosphonic acid [MDP],
hydroxymethylenediphosphonic acid (HMDP),
hydroxycyclohexylmethylenediphosphonic acid [HCMDP],
3-amino-1-hydroxypropane-1,1-diphosphonic acid [ADP],
aminotris(methylenephosphonic acid) [ATMP],
bis(dihydroxyphosphonylmethyl)aminoacetic acid [BPMAA],
iminobis(methylenephosphonic acid) [IBM],
alpha-amino(4-hydroxybenzylidene)diphosphonic acid [BDP3),
alpha-hydroxy(4-hydroxybenzylidene)diphosphonic acid [BDP4],
methylaminomethanediphosphonic acid [MAD],
aminoethanediphosphonic acid [AEDP],
phosphonoacetic acid [PAA],
3-phosphonopentane-1,3,5-tricarboxylic acid [PPTC], ethylenediaminetetramethylenephosphoric acid [EDMP],
azacycloheptanediphosphonic acid [AHP].

Anions of these phosphonic acids are indicated hereinafter by an H which is attached to the abbreviation and has a subscript negative index which specifies the number of protons lost. Thus, for example, APDH.$_{-2}$ means the doubly negatively charged anion of APD.

The following amines are suitable examples of the amine ligand $R^1NH_2$:

ammonia,
methylamine,
ethylamine,
propylamine,
isopropylamine,
butylamine,
hexylamine,
ethylenediamine,
1,2-diaminopropane,
amino acids such as, for example, glycine, alanine, valine, leucine, serine, ornithine, aspartic acid, phenylalanine or tyrosine,
cis-1,2-diaminocyclohexane,
cyclohexylamine,
1,1-bis(aminomethyl)cyclohexane,
and the like.

Preferred amines $R^1NH_2$ are ammonia, ethylamine, propylamine, isopropylamine, ethylenediamine, 1,2-diaminopropane, 1,2-diaminocyclohexane and 1,1-bis-(aminomethyl)cyclohexane.

Suitable examples of the singly negatively charged anion X are, besides hydroxide and chloride, also bromide, iodide, fluoride, nitrate, hydrogen sulphate, dihydrogen phosphate or anions of organic acids such as, for example, acetic acid, propionic acid, adipic acid, citric acid, gluconic acid, benzoic acid, butyric acid, maleic acid, lauric acid, malonic acid, fumaric acid, oxalic acid, tartaric acid, stearic acid, 2-hydroxy-3-naphthoic acid, cyclobutanedicarboxylic acid or benzenedi- and tri-carboxylic acids such as, for example, 1,2,4-benzenetricarboxylic acid, where A are in each case radicals of the phosphonic acids defined above, and "N(aminophosphonic acid)" denotes one of the phosphonic acids which is defined above and contains N groups.

The platinum complexes of the invention can be obtained by reacting a compound of the general formula III, III' or III"

$$[(R^1NH_2)_nPt]_qX_2 \quad (III)$$

$$[(R^{1'}NH_2)_{n'}Pt]_{q'}X''_2 \quad (III')$$

$$[(R^{1''}NH_2)_{n''}Pt]_{q''}X''_2 \quad (III'')$$

in which $R^1$, $R^{1'}$, $R^{1''}$, X, X', X", n, n', n", q, q' and q" have the above meanings,
with phosphonic acids of the general formula II, II' or II"

$$(HO)_2P(O)\text{—}R^2 \quad (II)$$

$$(HO)_2P(O)\text{—}R^{2'} \quad (II') \text{ or}$$

$$(HO)_2P(O)\text{—}R^{2''} \quad (II'')$$

in which $R^2$, $R^{2'}$ and $R^{2''}$ are as defined above or with bis-(dihydroxyphosphonylmethyl)-aminoacetic acid or phosphonic acids of the general formulae IV-VI $$R^4\text{—}C(R^5)(PO_3H_2)_2 \quad (IV)$$

in which $R^4$ denotes $C_1$-$C_3$-alkyl, optionally hydroxyl-substituted $C_5$-$C_6$-cycloalkyl, phenyl, hydroxyphenyl, halogen, $R^5R^6N$—$(CH_2)_r$—, where $R^5$ and $R^6$, which can be identical or different, denote hydrogen and/or $C_1$-$C_3$-alkyl and r denotes a number from 2 to 4, or denotes —CH(COOH)—CH$_2$—COOH, and
$R^5$ is hydrogen, hydroxyl, amino, mono- or di-$C_1$-$C_3$-alkylamino or $C_1$-$C_3$-alkyl, $$R^6\text{—}C(COOH)(R^7)(PO_3H_2) \quad (V)$$

in which $R^6$ denotes hydrogen, —CH$_2$—COOH or —CH$_2$—CH$_2$—COOH and $R^7$ denotes hydrogen, —CH$_2$—CH$_2$—COOH or —CH$_2$—CH(COOH)—CH$_2$—COOH, it also being possible for $R^4$ and $R^5$ to form an azacycloalkane ring having 4-6 carbon atoms and, where appropriate, a $C_1$-$C_3$-alkyl substituent on the N atom, or $$R^8\text{—}N(CH_2\text{—}PO_3H_2)_2 \quad (VI)$$

in which $R^8$ denotes —CH$_2$—PO$_3$H$_2$, —CH$_2$—COOH or —CH$_2)_s$—N(CH$_2$—PO$_3$H$_2$)$_2$, where s is a number from 2 to 6, or phosphonic acids of the general formulae IV-VI,
and if desired, converting into the salts of the pharmacologically acceptable acids and bases, and/or, if desired, oxidizing in the presence of a singly negatively charged anion of the meaning X,
or reacting a compound of the general formula $$PtX_4$$

in which X is as defined above, with the phosphonic acids of the general formulae II, II' and II" or with bis(dihydroxyphosphonylmethyl)-aminoacetic acid or with the phosphonic acids of the general formulae IV-VI and, where appropriate, reducing, as well as converting the reaction product, if desired, into the salts of pharmacologically acceptable acids and bases.

The reaction is preferably carried out in aqueous solution. The reaction is particularly advantageously carried out in the presence of silver(I) sulphate. It is furthermore advantageous to employ the phosphonic acids in the form of their alkali metal salts, in particular sodium salts.

The invention furthermore relates to the abovementioned process and to the variants mentioned in the description.

The reaction is preferably carried out in aqueous solution in a temperature range from 5° to 90° C., preferably at 15° to 60° C.

The oxidation is brought about with the oxidizing agents usual for the oxidation of platinum(II) to platinum(IV) compounds. For example, the oxidation is carried out using hydrogen peroxide, resulting in compounds of the formula I in which X has the meaning hydroxyl. If this is carried out in the presence of an acid, X in the resulting compounds of the formula I denotes an anion of the acid used. In the case of oxidation in the presence of hydrogen chloride, X in the resulting compounds of the formula I denotes chloro. It is also possible to bring about the oxidation, for example, by chlorine or bromine.

The compounds of the general formulae III, III' and III" can be obtained by reacting a compound $L_2PtZ_4$ in which L denotes hydrogen or alkali metal, and Z denotes halogen, preferably chlorine and bromine, with an amine $R^1NH_2$ in which $R^1$ has the meanings indicated above.

The compound $L_2PtZ_4$ is preferably tetrachloroplatinic(II) acid which can be obtained by dissolving platinum(II) dichloride in hydrochloric acid, or disodium or dipotassium tetrachloroplatinate(II).

Suitable as organic solvent for variant b) are highly polar solvents such as, in particular, dimethylformamide (DMF).

The products according to the invention produced on reaction of a compound of the formula II with a phosphonic acid are isolated either by concentrating the reaction mixture or by adding solvents.

Examples of platinum complexes of the invention which can be prepared using the process of the invention are as follows:

$(CH_3CH_2NH_2)_2Pt(Cl_2\text{-}MDPH_{-1})_2$,
$(cyclohexylamine)_2Pt(PPSH_{-2})$,
$Na_2[(NH_3)_2Pt(HEDPH_{-4})]$,
$Na_2[(NH_3)_2Pt(Cl_2\text{-}MDPH_{-4})]$,
$Na_2[(NH_2CH_2CH_2NH_2)Pt(HEDPH_{-4})]$,
$[1,1\text{-}di(aminomethyl)cyclohexane]Pt(DPDH_{-2})$,
$Na_2[(NH_3)_2Pt(APDH_{-1})(OH)]$,
$[(NH_3)_2Pt(MADH_{-2})]$,
$[(NH_3)_2Pt(BDP3H_{-2})]$,
$[(NH_3)_2Pt(ATMPH_{-2})]$,
$[(NH_3)_2Pt(BPMAAH_{-2})]$,
$[(NH_3)_2Pt(HEDP)Pt(NH_3)_2]$,
$[Pt(ATMP/ATMPH_{-1})_2]Cl_2$,
$[Pt(BPMAA/BPMAAH_{-1})_2]Cl_2$,
$[Pt(BDP_3)_2]Cl_2$.

The pharmaceuticals according to the invention are administered intravenously in particular, but also intramuscularly, intraperitoneally, subcutaneously or orally. External application is also possible. Administration is preferably by intravenous injection or intravenous infusion.

The pharmaceuticals are prepared by processes known per se, employing the compounds according to the invention as such or, where appropriate, in combination with suitable pharmaceutical vehicles. If the new pharmaceutical preparations contain pharmaceutical vehicles in addition to the active substance, the content of active substance in these mixtures is 0.1 to 99.5, preferably 0.5 to 95, % by weight of the total mixture.

Consistent with the invention, an active substance is used in any suitable formulation, with the precondition that the development or maintenance of adequate levels of active substance is guaranteed. This can be achieved, for example, by oral or parenteral administration in suitable doses. The pharmaceutical preparation of the active substance is advantageously in the form of unit doses suitable for the desired administration. A unit dose can be, for example, a tablet, a coated tablet, a capsule, a suppository or a measured volume of a powder, a granulate, a solution, an emulsion or a suspension.

A "unit dose" within the meaning of the present invention means a physically defined unit which contains an individual quantity of the active ingredient in combination with a pharmaceutical vehicle and whose content of active substance corresponds to a fraction or multiple of a therapeutic single dose. A single dose preferably contains the quantity of active substance which is administered at one administration and which usually corresponds to a whole, a half, a third or a quarter of a daily dose.

When only a fraction, such as one half or one quarter, of the unit dose is required for a single therapeutic administration, it is advantageous for the unit dose to be divisible, for example in the form of a tablet with a dividing groove.

The pharmaceutical preparations according to the invention can, when they are in the form of single doses and intended for administration, for example, to humans, contain about 0.1 to 500 mg, advantageously 10 to 200 mg and, in particular, 50 to 150 mg of active substance.

In general, in human medicine the active substance(s) are, in the case of oral administration, administered in a daily dose of 0.1 to 5, preferably 1 to 3, mg/kg of body weight, where appropriate in the form of several, preferably I to 3, individual doses to achieve the desired results. A single dose contains the active substance(s) in quantities of 0.1 to 5, preferably 1 to 3, mg/kg of body weight. Similar dosages can be used in the case of oral treatment.

The therapeutic administration of the pharmaceutical preparation can take place 1 to 4 times a day at fixed or varying times, for example in each case before meals and/or in the evening. However, it may be necessary to deviate from the said dosages, specifically depending on the nature, the body weight and the age of the individual to be treated, the nature and severity of the disease, the nature of the preparation and the administration of the pharmaceutical, as well as the period or interval within which administration takes place. Thus, it may suffice in some cases to manage with less than the abovementioned quantity of active substance, whereas in other cases the abovementioned quantity of active substance must be exceeded. It may also prove expedient to administer the pharmaceutical only once or at an interval of several days.

The optimal dosage and mode of administration of the active substances necessary in each case can be established by anyone skilled in the art on the basis of his expert knowledge.

As a rule, the pharmaceutical preparations consist of the active substances according to the invention and nontoxic, pharmaceutically tolerated medicinal vehicles which are used as additive or diluent for the therapeutically active ingredient, for example in the form of a capsule, a tablet coating, a sachet or another container. A vehicle can act, for example, to promote absorption of the pharmaceutical by the body, as a formulating auxiliary, as a sweetener, as a masking flavour, as a colorant or as a preservative.

Possible for oral use are, for example, tablets, coated tablets, hard and soft capsules, for example composed of gelatin, dispersible powders, granules, aqueous and oily suspensions, emulsions, solutions or syrups.

Tablets can contain inert diluents, for example calcium carbonate, calcium phosphate, sodium phosphate or lactose; granulating and dispersing agents, for example maize starch or alginates; binders, for example starch, gelatin or gum acacia, and lubricants, for example aluminium stearate or magnesium stearate, talc or silicone oil. They can additionally be provided with a coating which may also have a nature such that it brings about delayed dissolution and absorption of the pharmaceutical in the gastrointestinal tract so that, for example, an improved tolerability, protraction or a delayed action is achieved. Gelatin capsules can contain the medicinal substance mixed with a solid, for example calcium carbonate or kaolin, or an oily, for example olive, arachis or paraffin oil, diluent.

Aqueous suspensions, which are prepared shortly before use where appropriate, can contain suspending agents, for example sodium carboxymethylcellulose, methylcellulose, hydroxypropylcellulose, sodium alginate, polyvinylpyrrolidone, gum tragacanth or gum acacia; dispersing and wetting agents, for example polyoxyethylene stearate, heptadecaethyleneoxycetanol, polyoxyethylene sorbitol monooleate, polyoxyethylene sorbitan monooleate or lecithin; preservatives, for example methyl or propyl hydroxybenzoates; flavourings; sweeteners, for example sucrose, lactose, sodium cyclamate, dextrose, invert sugar syrup.

Oily suspensions can contain, for example, arachis, olive, sesame, coconut or paraffin oil and thickeners, such as, for example, beeswax, hard paraffin or cetyl alcohol; also sweeteners, flavourings and antioxidants.

Powders and granules which can be dispersed in water can contain a compound according to the invention mixed with dispersing, wetting and suspending agents, for example the abovementioned, as well as with sweeteners, flavourings and colorants.

Emulsions can contain, for example, olive, arachis or paraffin oil in addition to emulsifiers such as, for example, gum acacia, gum tragacanth, phosphatids, sorbitan monooleate, polyoxyethylene sorbitan monooleate, and sweeteners and flavourings.

The active substances can, where appropriate, also be formulated in microencapsulated form with one or more of the vehicles or additives indicated.

The invention is explained in more detail hereinafter by means of preferred exemplary embodiments.

It is expedient to use for the preparation in the following examples an activated cisplatin solution which is prepared as follows: 1 mmol of cisplatin is dissolved in water; then 0.98 mmol of $Ag_2SO_4$ dissolved in water is added. The mixture is subsequently shaken at room temperature, protected from light, for 24 h, and AgCl is filtered off. 0.96 mmol of $Ba(OH)_2$ are dissolved in water and added. The mixture is then shaken at room temperature, protected from light, for 24 h, and $BASO_4$ is filtered off. The resulting solution is activated cisplatin solution.

EXAMPLE 1

Disodium diammine(1-hydroxyethane-1,1-diphosphonato)-platinate(II), $Na_2[(NH_3)_2Pt(HEDPH_4)]$ The title compound is prepared by reacting $Na_2$-$HEDPH_{-2}$ with activated cisplatin solution. A sand-coloured product is obtained.

EXAMPLE 2

Disodium diammine(dichloromethanediphosphonato)-platinate(II), $Na_2[(NH_3)_2Pt(Cl_2\text{-}MDPH_4)]$ The title compound is prepared by reacting $Na_2MDPH_{-2}$ with activated cisplatin solution. A sand-coloured product is obtained.

EXAMPLE 3

$cis[Pt(NH_3)_2(Na_2\text{-}APDH_{-1})(OH)] \times 2H_2O$ 2 mmol of $Na_2APD \times 2H_2O$ are dissolved in 50 ml of $H_2O$; then 2 mmol of activated cisplatin solution are added, resulting in slight turbidity. Solvent is subsequently removed in a rotary evaporator at 50° C. This results in a clear yellow solution. After the solvent has been completely removed in a rotary evaporator there remains an ivory-coloured powder which is dried over a desiccant.

EXAMPLE 4

$cis[Pt(NH_3)_2(MADH_{-2})]$ 4 mmol of MAD are dissolved in 50 ml of $H_2O$. To this are added 4 mmol of activated cisplatin solution, resulting in a white flocculent turbidity which cannot be filtered. The mixture is then heated to 50° C., resulting in a clear yellow solution. The solvent is removed in a rotary evaporator, resulting in a green-coloured product which is dried over a desiccant.

EXAMPLE 5

$cis[Pt(NH_3)_2(BDP3H_{-2})] \times 3H_2O$ 4 mmol of BDP-3 are dissolved in 100 ml of $H_2O$. 4 mmol of activated cisplatin solution are subsequently added, resulting in a white precipitate which is filtered off with suction, washed with water and subsequently dried over a desiccant.

EXAMPLE 6

$cis[Pt(NH_3)_2(ATMPH_{-2})]$ 2 mmol of ATMP are dissolved in 25 ml of $H_2O$ and subsequently 2 mmol of activated cisplatin solution are added. The solution is stirred at 50° C. for one hour, the solvent is removed in a rotary evaporator, and the compound is obtained as a cream-coloured powder.

EXAMPLE 7

$cis[Pt(NH_3)_2 (BPMAAH_{-2})]$ 2 mmol of BPMAA are dissolved in 30 ml of $H_2O$. 2 mmol of activated cisplatin solution are subsequently added, and the mixture is stirred at 50° C. for one hour. Solvent is subsequently removed in a rotary evaporator, and the residue is dried over a desiccant.

EXAMPLE 8

$[(NH_3)_2Pt(HEDP)Pt(NH_3)_2]$ 2 mmol of $Na_2HEDP$ are dissolved in 50 ml of $H_2O$ and subsequently 2 mmol of activated cisplatin solution are added. A whitish turbidity forms. The mixture is subsequently stirred at 50° C. for one hour, resulting in a yellow precipitate, which is filtered off with suction, washed with water and dried over a desiccant. A yellow-green product is obtained.

The starting material in the following examples is not activated cisplatin solution but platinum tetrachloride ($PtCl_4$). In contrast to the above examples, the platinum in this is in the +IV, not +II, oxidation state. The preferential product of the reaction is a PT(II) bond; however, it is also possible for PT(IV) products to be formed.

EXAMPLE 9

$cis[Pt(Cl_2)(ATMP/ATMPH_{-1})_2]$ 2 mmol of $PtCl_2$ are dissolved in 20 ml of $H_2O$, to this are added 4 mmol of ATMP dissolved in 40 ml of $H_2O$ and the mixture is stirred at 50° C., protected from light, for 3 hours. The solvent is subsequently removed from the solution in a rotary evaporator, and the residue is dried under high vacuum at 50° C. for 2 hours. A dark green hygroscopic substance is obtained.

EXAMPLE 10 cis[PtCl$_2$(BPMAA/BPMAAH.$_1$)$_2$]

1 mmol of PtCl$_4$ is dissolved in 10 ml of H$_2$O. To this are added 2 mmol of BPMAA dissolved in 20 ml of H$_2$O. The solution is heated to reflux at 50° C. for 1 hour, the solvent is subsequently removed in a rotary evaporator, and the residue is dried at 50° C. under high vacuum for two hours. An orange-brown substance is obtained.

EXAMPLE 11 cis[PtCl$_2$(BDP3)$_2$]

4 mmol of BDP-3 are dissolved in 200 ml of H$_2$O to this are added 2 mmol of PtCl$_4$ dissolved in 20 ml of H$_2$O and the mixture is stirred at 50° C. for 3 hours. The solvent is subsequently removed in a rotary evaporator, and the residue is dried at 50° C. under high vacuum for 2 hours and additionally dried in a desiccator over a desiccant and KOH overnight. A green substance is obtained. The analogous (BDP4)-Pt complex is prepared correspondingly.

EXAMPLE 12 cis-[Diammineazocycloheptane-2,2-disphosphonato-platinum-(II)] cis[Pt(AHP)(NH$_3$)$_2$]

2 mole of AHP were dissolved by heating in 150 ml of water. 25 ml of an activated cisplatin solution (2 mmol) were added. The solution became yellow and gradually turbid. The solvent was removed in a rotary evaporator and the residue was dried over a desiccant. The grey-green compound was characterized by elemental analysis and $^{31}$P NMR spectroscopy.

EXAMPLE 13 cis-[Imino-bis(methylenephosphonato)diammino-platinum(II)] cis[Pt(IBM)(NH$_3$)$_2$]

2 mmol of IBM were dissolved in 50 ml of water. 25 ml of an activated cisplatin solution (2 mmol) were added; the solution became pale yellow and slightly turbid. Stirring at 50° C. for 1 h was followed by removal of the solvent in a rotary evaporator, and the product was dried over a desiccant. The creamy white compound was characterized by elemental analysis and by $^{31}$P NMR spectroscopy.

What is claimed is:

1. A pharmaceutical preparation comprising at least 0.5% by weight of a pharmaceutical vehicle and also comprising a platinum complex or a salt, with a pharmacologically acceptable acid or base, of said platinum complex, wherein said platinum complex has the general formula I:

$$\{(R^1NH_2)_nPt\}_qYX_p \text{ TM (I),}$$

in which:
(A) R$^1$NH$_2$ is selected from the group consisting of NH$_3$, methylamine, ethylamine, propylamine, isopropylamine, butylamine, hexylamine, cyclohexylamine, ethylenediamine, 1,2-diaminopropane, cis 1,2-diaminocyclohexane, and 1,1-bis(aminomethyl)cyclohexane;
(B) Y is selected from the group consisting of:
(a) phosphonic acids of the general formula II:

$$R^2—C(R^3)—(PO_3H_2)_2 \text{ TM (II),}$$

in which:
(i) R$^2$ is selected from the group consisting of:
(i.1) hydrogen, (i.2) C$_1$-C$_3$ alkyl, (i.3) C$_5$-C$_6$ cycloalkyl, (i.4) hydroxyl substituted C$_5$-C$_6$ cycloalkyl, (i.5) phenyl, (i.6) hydroxy phenyl, (i.7) halogen, (i.8) —CH(COOH)—CH$_2$—COOH, and (i.9) R$^4$R$^5$N—(CH$_{2r}$—, where (i.9.1) each of R$^4$ and R$^5$ independently denotes (i.8.1.1) a hydrogen or (i.8.1.2) a C$_1$-C$_3$ alkyl group; and (i.9.2) r denotes an integer from 2 to 4; and
(ii) R$^3$ is amino or mono- or di-C$_1$-C$_3$ alkylamino; and
(b) phosphonic acids of the general formula III:

$$R^6—N(CH_2—PO_3H_2)_2 \quad (III),$$

in which R$^6$ is selected from the group consisting of (i) —CH2—PO3H2, (ii) —CH2—COOH, and (iii) —(CH$_2$)$_s$—N(CH$_2$—PO$_3$H$_2$)$_2$, where s is a number from 2 to 6,
(c) iminobis(methylenephosphonic acid);
(d) ethylenediaminetetramethylenephosphonic acid; and
(e) azacycloheptanediphosphonic acid;
(C) X denotes a singly negatively charged anion;
(D) n denotes one of the numbers 0, 1, or 2, but denotes the number 1 only if R$^1$ has a nitrogen functionality which is able to coordinate with the central Pt ion;
(E) p denotes one of the numbers 0 or 2, but denotes the number 2 only if the Pt is in oxidation state IV; and
(F) q denotes the number 1 or 2 if n is not zero and the number 1 if n is 0.

2. A pharmaceutical preparation according to claim 1 comprising a sodium salt of a platinum complex according to formula (I).

3. A pharmaceutical preparation according to claim 2, wherein Y is selected from the group consisting of 3-amino-1-hydroxypropane-1,1-diphosphonic acid, aminotris(methylenephosphonic acid), bis(dihydroxyphosphonylmethyl)aminoacetic acid, iminobis(methylenephosphonic acid), alpha-amino(4-hydroxybenzylidene)diphosphonic acid, methylaminomethanediphosphonic acid, aminoethanediphosphonic acid, ethylenediaminetetramethylenephosphonic acid, and azacycloheptanediphosphonic acid.

4. A pharmaceutical preparation according to claim 1, wherein Y is selected from the group consisting of 3-amino-1-hydroxypropane-1,1-diphosphonic acid, aminotris(methylenephosphonic acid), bis(dihydroxyphosphonylmethyl)aminoacetic acid, iminobis(methylenephosphonic acid), alpha-amino(4-hydroxybenzylidene)diphosphonic acid, methylaminomethanediphosphonic acid, aminoethanediphosphonic acid, ethylenediaminetetramethylenephosphonic acid, and azacycloheptanediphosphonic acid.

5. A pharmaceutical preparation according to claim 4, wherein X is selected from the group consisting of hydroxide, chloride, bromide, iodide, fluoride, nitrate, hydrogen sulfate, dihydrogen phosphate, acetate, propionate, hydrogen adipate, dihydrogen citrate, gluconate, benzoate, butyrate, hydrogen maleate, laurate, hydrogen malonate, hydrogen fumarate, hydrogen oxalate, hydrogen tartrate, stearate, 2-hydroxy-3-naphthoate, hydrogen cyclobutanedicarboxylate, and dihydrogen 1,2,4-benzenetricarboxylate.

6. A pharmaceutical preparation according to claim 3, wherein X is selected from the group consisting of hydroxide, chloride, bromide, iodide, fluoride, nitrate, hydrogen sulfate, dihydrogen phosphate, acetate, propionate, hydrogen adipate, dihydrogen citrate, gluconate, benzoate, butyrate, hydrogen maleate, laurate, hydrogen malonate, hydrogen fumarate, hydrogen oxalate, hydrogen tartrate, stearate, 2-hydroxy-3-naphthoate, hydrogen cyclobutanedicarboxylate, and dihydrogen 1,2,4-benzenetricarboxylate.

7. A pharmaceutical preparation according to claim 2, wherein X is selected from the group consisting of hydroxide, chloride, bromide, iodide, fluoride, nitrate, hydrogen sulfate, dihydrogen phosphate, acetate, propionate, hydrogen adipate, dihydrogen citrate, gluconate, benzoate, butyrate, hydrogen maleate, laurate, hydrogen malonate, hydrogen fumarate, hydrogen oxalate, hydrogen tartrate, stearate, 2-hydroxy-3-naphthoate, hydrogen cyclobutanedicarboxylate, and dihydrogen 1,2,4-benzenetricarboxylate.

8. A pharmaceutical preparation according to claim 1, wherein X is selected from the group consisting of hydroxide, chloride, bromide, iodide, fluoride, nitrate, hydrogen sulfate, dihydrogen phosphate, acetate, propionate, hydrogen adipate, dihydrogen citrate, gluconate, benzoate, butyrate, hydrogen maleate, laurate, hydrogen malonate, hydrogen fumarate, hydrogen oxalate, hydrogen tartrate, stearate, 2-hydroxy-3-naphthoate, hydrogen cyclobutanedicarboxylate, and dihydrogen 1,2,4-benzenetricarboxylate.

9. A process for treating tumours which are susceptible thereto which comprises administering to a human subject a pharmaceutical comprising a platinum complex or a salt, with a pharmacologically acceptable acid or base, of said platinum complex, wherein said platinum complex has the general formula I:

$$\{(R^1NH_2)_nPt\}_q YX_p \text{ TM (I)},$$

in which:
(A) $R^1NH_2$ is selected from the group consisting of $NH_3$ methylamine, ethylamine, propylamine, isopropylamine, butylamine, hexylamine, cyclohexylamine, ethylenediamine, 1,2-diaminopropane, cis 1,2-diaminocyclohexane, and 1,1-bis (aminomethyl)cyclohexane;
(B) Y is selected from the group consisting of:
 (a) phosphonic acids of the general formula II:

$$R^2—C(R^3)—(PO_3H_2)_2 \text{ TM (II)},$$

in which:
 (i) $R^2$ is selected from the group consisting of: (i.1) hydrogen, (i.2) $C_1$-$C_3$ alkyl, (i.3) $C_5$-$C_6$ cycloalkyl, (i.4) hydroxyl substituted $C_5$-$C_6$ cycloalkyl, (i.5) phenyl, (i.6) hydroxy phenyl, (i.7) halogen, (i.8) —CH(COOH)—CH$_2$—COOH, and (i.9) $R^4R^5N$—(CH$_2$)$_r$—, where (i.9.1) each of $R^4$ and $R^5$ independently denotes (i.8.1.1) a hydrogen or (i.8.1.2) a $C_1$-$C_3$ alkyl group; and (i.9.2) r denotes an integer from 2 to 4; and
 (ii) $R^3$ is amino or mono- or di-$C_1$-$C_3$ alkylamino; and
(b) phosphonic acids of the general formula III:

$$R^6—N(CH_2—PO_3H_2)_2 \text{ TM (III)},$$

in which $R^6$ is selected from the group consisting of (i) —CH2—PO3H2, (ii) —CH2—COOH, and (iii) —(CH$_2$)$_s$—N(CH$_2$—PO$_3$H$_2$)$_2$, where s is a number from 2 to 6,
(c) iminobis(methylenephosphonic acid);
(d) ethylenediaminetetramethylenephosphonic acid; and
(e) azacycloheptanediphosphonic acid;
(C) X denotes a singly negatively charged anion;
(D) n denotes one of the numbers 0, 1, or 2, but denotes the number 1 only if $R^1$ has a nitrogen functionality which is able to coordinate with the central Pt ion;
(E) p denotes one of the numbers 0 or 2, but denotes the number 2 only if the Pt is in oxidation state IV; and
(F) q denotes the number 1 or 2 if n is not zero and the number 1 if n is 0.

10. A process according to claim 9, wherein the pharmaceutical comprises a sodium salt of a platinum complex according to formula (I).

11. A process according to claim 10, wherein Y is selected from the group consisting of 3-amino-1-hydroxypropane-1,1-diphosphonic acid, aminotris(methylenephosphonic acid), bis(dihydroxyphosphonylmethyl)aminoacetic acid, iminobis(methylenephosphonic acid), alpha-amino(4-hydroxybenzylidene)diphosphonic acid, methylaminomethanediphosphonic acid, aminoethanediphosphonic acid, ethylenediaminetetramethylenephosphonic acid, and azacycloheptanediphosphonic acid.

12. A process according to claim 9, wherein Y is selected from the group consisting of 3-amino-1-hydroxypropane-1,1-diphosphonic acid, aminotris(methylenephosphonic acid), bis(dihydroxyphosphonylmethyl)aminoacetic acid, iminobis(methylenephosphonic acid), alpha-amino(4-hydroxybenzylidene)diphosphonic acid, methylaminomethanediphosphonic acid, aminoethanediphosphonic acid, ethylenediaminetetramethylenephosphonic acid, and azacycloheptanediphosphonic acid.

13. A process according to claim 12, wherein X is selected from the group consisting of hydroxide, chloride bromide, iodide, fluoride, nitrate, hydrogen sulphate, dihydrogen phosphate, acetate, propionate, hydrogen adipate, dihydrogen citrate, gluconate, benzoate, butyrate, hydrogen maleate, laurate, hydrogen malonate, hydrogen fumarate, hydrogen oxalate, hydrogen tartrate, stearate, 2-hydroxy-3-naphthoate, hydrogen cyclobutanedicarboxylate, and dihydrogen 1,2,4-benzenetricarboxylate.

14. A process according to claim 11, wherein X is selected from the group consisting of hydroxide, chloride, bromide, iodide, fluoride, nitrate, hydrogen sulphate, dihydrogen phosphate, acetate, propionate, hydrogen adipate, dihydrogen citrate, gluconate, benzoate, butyrate, hydrogen maleate, laurate, hydrogen malonate, hydrogen fumarate, hydrogen oxalate, hydrogen tartrate, stearate, 2-hydroxy-3naphthoate, hydrogen cyclobutanedicarboxylate, and dihydrogen 1,2,4-benzenetricarboxylate.

15. A process according to claim 10, wherein X is selected from the group consisting of hydroxide, chloride, bromide, iodide, fluoride, nitrate, hydrogen sulphate, dihydrogen phosphate, acetate, propionate, hydrogen adipate, dihydrogen citrate, gluconate, benzoate, butyrate, hydrogen maleate, laurate, hydrogen malonate, hydrogen fumarate, hydrogen oxalate, hydrogen tartrate, stearate, 2-hydroxy-3-naphthoate, hydrogen cyclobutanedicarboxylate, and dihydrogen 1,2,4-benzenetricarboxylate.

16. A process according to claim 9, wherein X is selected from the group consisting of hydroxide, chloride, bromide, iodide, fluoride, nitrate, hydrogen sulphate, dihydrogen phosphate, acetate, propionate, hydrogen adipate, dihydrogen citrate, gluconate, benzoate, butyrate, hydrogen maleate, laurate, hydrogen malonate, hydrogen fumarate, hydrogen oxalate, hydrogen tartrate, stearate, 2-hydroxy-3-naphthoate, hydrogen cyclobutanedicarboxylate, and dihydrogen 1,2,4-benzenetricarboxylate.

17. A process according to claim 13, wherein the pharmaceutical is administered intravenously.

18. A process according to claim 12, wherein the pharmaceutical is administered intravenously.

19. A process according to claim 10, wherein the pharmaceutical is administered intravenously.

20. A process according to claim 9, wherein the pharmaceutical is administered intravenously.

* * * * *